(12) United States Patent
Garcia-Mina Freire et al.

(10) Patent No.: US 7,795,180 B2
(45) Date of Patent: Sep. 14, 2010

(54) USE FOR 2-HYDROXY-4-METHYLTHIOBUTANOIC ACID (HMTB)

(75) Inventors: Jose Maria Garcia-Mina Freire, Iza (ES); D. Fabrice Houdusse, Medigorria (ES); Esther Casanova, Pamplona (ES); Maria Garnica, Pamplona (ES)

(73) Assignee: Timac Agro Espana, S.A., Navarra (ES)

( * ) Notice: Subject to any disclaimer, the term of this patent is extended or adjusted under 35 U.S.C. 154(b) by 0 days.

(21) Appl. No.: 11/788,128

(22) Filed: Apr. 19, 2007

(65) Prior Publication Data
US 2007/0249499 A1    Oct. 25, 2007

(30) Foreign Application Priority Data
Apr. 25, 2006    (ES) ............................. 200601056

(51) Int. Cl.
*A01N 37/36*    (2006.01)
*A01N 37/44*    (2006.01)

(52) U.S. Cl. ................................. 504/319
(58) Field of Classification Search ................. 504/319
See application file for complete search history.

(56) References Cited

FOREIGN PATENT DOCUMENTS

| DE | EP 0965269 | * 12/1999 |
|---|---|---|
| ES | 465883 | 7/1978 |
| ES | 200600178 | 1/2006 |
| JP | 61204121 | 9/1986 |

OTHER PUBLICATIONS

Regina Berjano2, Clara de Vega, Montserrat Arista, Pedro L. Ortiz and Salvador Talavera, "A multi-year study of factors affecting fruit production in *Aristolochia paucinervis* (Aristolochiaceae)1" American Journal of Botany. 2006;93:599-606. Received for publication Jul. 4, 2005. Accepted for publication Jan. 24, 2006.*

* cited by examiner

*Primary Examiner*—Frederick Krass
*Assistant Examiner*—Ben Packard
(74) *Attorney, Agent, or Firm*—John C. McMahon

(57) ABSTRACT

A new use of 2-hydroxy-4-methylthiobutanoic acid (HMTB) as an inducer, within the plant, of ethylene and polyamine synthesis, mainly putrescine, capable of regulating fruit maturation processes, both in relation to fruit abscission and in relation to color and sugar content, containing mineral elements such as phosphorous, potassium and nitrogen.

15 Claims, 1 Drawing Sheet

USE FOR 2-HYDROXY-4-METHYLTHIOBUTANOIC ACID (HMTB)

Figure 1:
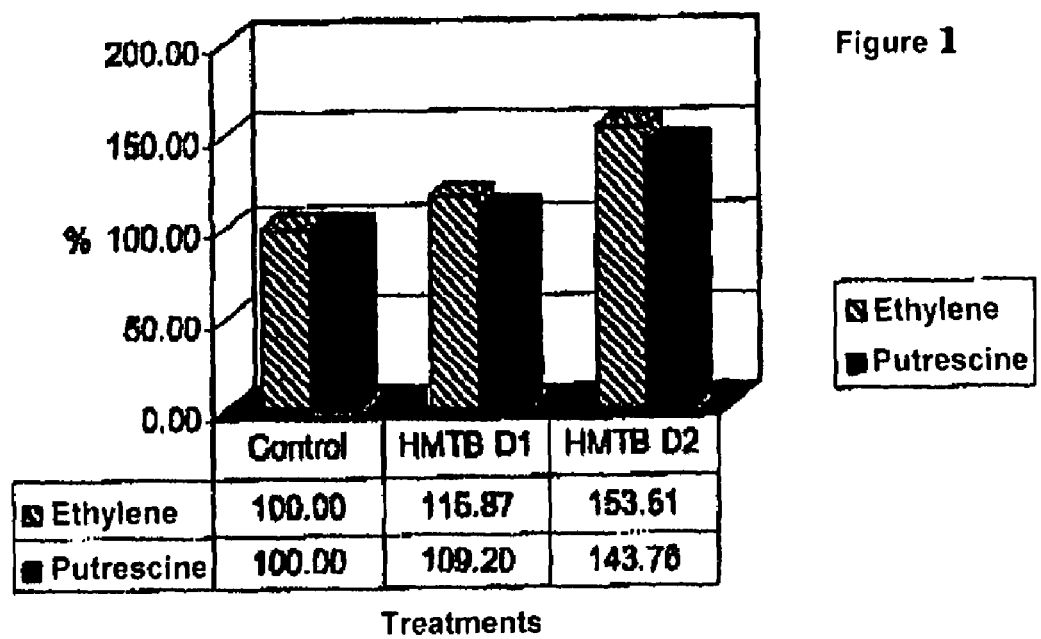

The present invention refers to a new agent that controls endogenous production of polyamines and ethylene in plants and the metabolic processes related to these phytoregulators, mainly senescence, abscission, color and maturation.

BACKGROUND OF THE INVENTION

Control of the maturation processes of fruits, as well as the physiological processes associated with maturation such as fruit abscission, sugar levels, or fruit color are very important in some crops such as for example vines (level and color) or olives (introduction of abscission for more efficient collection).

There are currently in the market substances that allow the generation of ethylene within the plant (Etefon, etheral). These substances are difficult to handle and may in fact produce important disorders in crops due to ethylene production not being controlled by the plant. It also has important problems relating to waste and safety periods. Compounds have also been used (derived from sulphonic acids) with the capacity to control maturation and abscission processes, for example in olives and citrics, but which do not describe whether they act upon ethylene or polyamine synthesis (ES465883). No patents have been found describing and protecting the capacity of HMTB to induce plant synthesis of ethylene and polyamines, and therefore to act upon fruit maturing processes such as fruit abscission, fruit color or sugar content. In fact, formulations containing this molecule as a main ingredient have proved to be very efficient in applications such as inducing olive abscission (which implies greater efficiency in fruit collection) or inducing sugar content and color in vines.

There are other products that have also been used such as 1-amine-cyclopropane carboxylic acid (JP61204121), which act upon plant ethylene synthesis.

The main problem experienced by these compounds is that together with the effects on maturation and abscission there are important side effects that consist in:

Causing the falling of leaves by acting only upon ethylene concentration.
Presence of waste.
Negatively affecting subsequent fruit preservation.

A patent has also been filed including the effect of HMTB as an activator of mineral nutrient assimilation in plants and of metabolic processes associated to this greater increase in nutrient assimilation, such as for example protein synthesis, chlorophyll synthesis and photosynthesis (P200600178).

Subsequent studies performed in our laboratory have shown that HMTB (and derivatives), as well as being an effective nutritional activator, are capable of acting upon the internal balance of ethylene and polyamines. This last and novel effect is completely different to that described in patent P200600178 since this new effect claimed—induction of the endogenous synthesis of ethylene and putrescine—does not have any effect on nutrient assimilation. That is, the effect claimed in P200600178 (nutritional activator) is caused by different mechanisms to the effect claimed in the present patent.

DESCRIPTION OF THE INVENTION

This invention describes the efficiency of 2-hydroxy-4-methylthiobutanoic acid (HMTB) as an inducer in synthesizing ethylene and polyamine, mainly putrescine, in plants, and therefore as an agent capable of regulating fruit maturation processes, both in relation to fruit abscission and to color and sugar content.

The advantage of the present product with respect to all that described above is that it does not produce waste, since it is in itself beneficial food for animals and humans. Likewise, it has minimum negative effects upon leaf fall, since the simultaneous synthesis of ethylene and putrescine, which is furthermore controlled by the plant, preserves the plant from the imbalances characteristic of exclusive ethylene synthesis. Likewise, the presence of putrescine allows controlling the negative effects on fruit preservation associated to the excess in ethylene.

On the other hand, the new effect of HMTB and analogues claimed in this patent (induction of endogenous synthesis of ethylene and putrescine) is also important, since it contributes to controlling maturation processes such as color and sugar content and fruit abscission. These new effects of HMTB can be important for example in the color and sugar levels of grapes and the wines they produce, color and sugar content of fruits or collection of fruits such as for example in the case of pitted fruits and citrics, and especially in the case of olives for which this process is critical since it allows mechanized collection, much more profitable than manual collection.

The present invention describes new formulations containing the compound 2-hydroxy-4-methylthiobutanoic acid (HMTB) (D and L isomers), its salts, esters, amides or ethers in position 2, according to formula I,

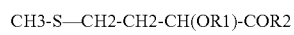

$$CH3-S-CH2-CH2-CH(OR1)-COR2 \qquad I$$

wherein R1 is selected from the group consisting of hydrogen, alkyl moieties (preferably methyl or ethyl) and aryl; whereas R2 is selected from the group consisting of hydroxyl, amides and esters of alkyl moieties (preferably methyl or ethyl) or aryl. When the moiety is hydroxyl, salts of the acid with monovalent (preferably $Na^+$ and $K^+$) and polyvalent (preferably $Ca^{++}$, $Mg^{++}$, $Cu^{++}$ and $Fe^{+++}$) cations are also considered, as well as with electropositive organic compounds such as amines (for example ethanolamine).

Formulations containing one or several of the components contained in formula I can be formulated accompanied by mineral nutrients (preferably phosphorous and potassium) or other biostimulant (such as, for example, amino acids, humic and/or fulvic substances, algae extracts and/or lignosulphonates) and/or phytoregulating (such as for example auxines, cytokines, nitric oxide or nitric oxide precursors, salicylic acid, polyamines, other ethylene precursors, gibberellins and brassinosteroids) organic molecules.

In these formulations HMTB can be formulated at any concentration, the preferred concentration interval being between 1 and 40%.

In these formulations the mineral nutrients (such as, for example, nitrogen, phosphorous, potassium, magnesium, calcium, iron, boron, zinc, manganese and molybdenum) can be introduced at any concentration, the preferred concentration being between 1 and 20%.

In these formulations the biostimulant and/or regulating products can be introduced at any concentration, the preferred concentration being between 1 and 10%.

Liquid formulations can be manufactured by the simple mixture of the different constituents in a reactor-stirrer at any temperature, although the optimum temperature would be that between 20-30° C., and pressure, although the optimum pressure would be atmospheric pressure.

Solid formulations can be manufactured by means of mixing the different solid components in a paddle stirrer or a Lodige stirrer, at room temperature and pressure. The product can be presented in liquid or solid phase. The solid presentation can be obtained by means of liquid product absorption in clays such as sepiolite, zeolite, stapuigite or bentonite; or using solid sources of HMTB such as for example calcium salt.

Our studies indicate that HMTB and analogues act upon the maturation process by means of the increase in endogenous polyamine synthesis, mainly putrescine and ethylene. This effect is mediated by its capacity to increase the endogenous concentration of S-adenosyl-methionine, the common precursor of putrescine and ethylene.

FIG. 1 shows how the HTMB application in pepper plants causes simultaneous increase in ethylene and putrescine. This effect was directly related to increases in the number of fruits and in fruit coloration (more advanced maturation state) (FIG. 2).

FIG. 1 shows the effect of HMTB according to the formulation of Example 1 on ethylene and putrescine production in pepper leaves treated on the leaves. Measurements were performed 7 days after applying the product. HMTB D1 is 100 mg/l of solution and D2 is 1 g/l of solution.

Figure 2:
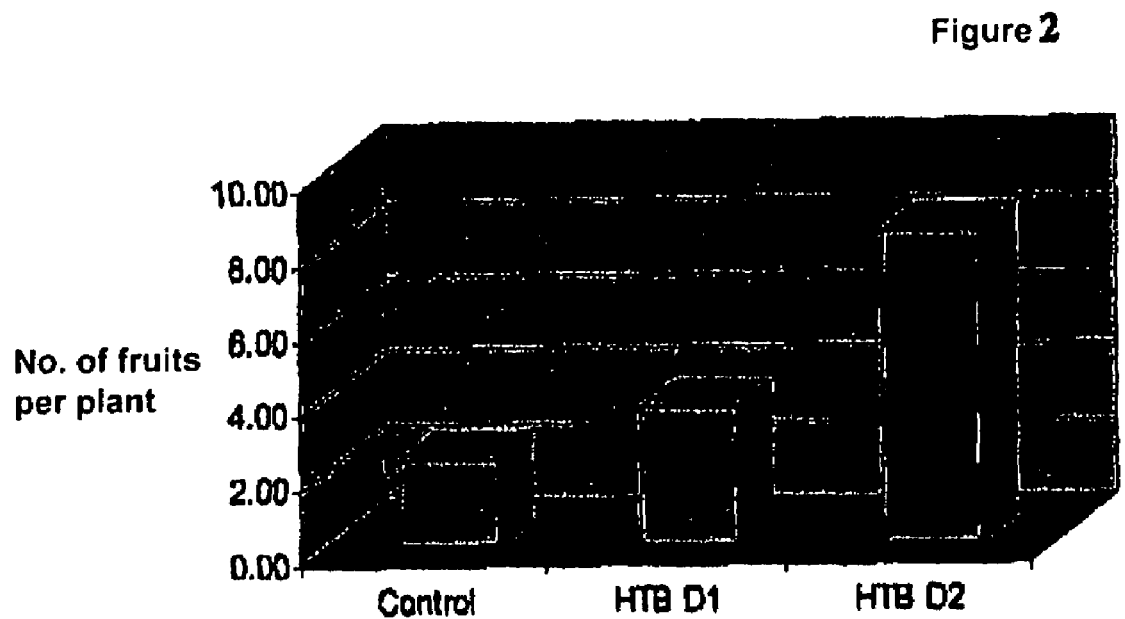

FIG. 2 shows the effect of leaf application of HMTB according to the formulation of Example 1 on the number of fruits per plant in a pepper culture. Measurements were taken 45 days after applying the product. HMTB D1 is 100 mg/l of solution and D2 is 1 g/l of solution.

Formulations containing HMTB can be applied by root and leaf route, although the most notable effect on maturation is via leaf route at fruit veraison (when the fruit starts to change color).

Recommended doses are between 1 and 5 g per liter of active ingredient, although significant effects have been recorded at lower doses such as 100 mg per liter, for example.

FORMULATION EXAMPLES

Example 1

Liquid Formulation

40% HMTB
60% water

Example 2

Liquid Formulation

40% HMTB
20% monopotassium phosphate
40% water

Example 3

Liquid Formulation

25% HMTB
25% of 85% phosphoric acid
5% potassium hydroxide (95%)
45% water

Example 4

Liquid Formulation

40% HMTB
20% diammonium phosphate
10% water
10% sugar cane vinasse

Example 5

Solid Formulation

40% HMTB calcium salt
60% monoammonium phosphate

Example 6

Solid Formulation

40% HMTB calcium salt
60% monopotassium phosphate

The invention claimed is:

1. A method to control fruit maturing processes by inducing the synthesis of ethylene and polyamine, the method comprising the steps of:
   (a) applying a formulation to the leaves of fruiting plants;
   (b) wherein the formulation contains a component selected from the group consisting of 2-hydroxy-4-methylthiobutanoic acid, a salt of 2-hydroxy-4-methylthiobutanoic acid, an ester of 2-hydroxy-4-methylthiobutanoic acid, an amide of 2-hydroxy-4-methylthiobutanoic acid and an ether of 2-hydroxy-4-methylthiobutanoic acid, wherein the 2-hydroxy-4-methylthiobutanoic acid has a structure according to the formula CH3-S—CH2-CH 2CH(OR1)—COR2;
   (c) wherein R1 is selected from the group consisting of hydrogen, alkyl moieties and aryl moieties;
   (d) R2 is selected from the group consisting of hydroxyl moieties, amides of alkyl moieties, esters of alkyl moieties and aryl moieties; and
   (e) wherein the hydroxyl moiety is an OX moiety and X is selected from the group consisting of monovalent cations, and polyvalent cations.

2. The method according to claim 1 wherein a dose of the formulation applied is 100 mg/L to 5 gr/l.

3. The method according to claim 1, in which the formulation applied comprises between 1% and 40% of the component and the remainder of the formulation is at least one member selected from the group consisting of water, mineral nutrients, biostimulating organic molecules, and phytoregulating organic molecules.

4. The method according to claim 3, wherein the formulation contains between 1% to 20% mineral nutrients.

5. The method according to claim 3, wherein the formulation contains between 1% to 10% of a compound selected from the group consisting of biostimulating organic molecules and phytoregulating organic molecules.

6. The method according to claim 3, wherein the formulation contains at least one mineral nutrient selected from the group consisting of phosphorous, potassium and nitrogen.

7. The method according to claim 3, wherein the formulation contains at least one biostimulating organic molecule selected from the group consisting of amino acids, algae extracts and lignosulphonates.

8. The method according to claim 3, wherein the formulation contains at least one phytoregulating organic molecule selected from the group consisting of auxines, salicylic acid, polyamines, cytokines, gibberellins and brassinosteriods.

9. The method according to claim 1 including the step of applying the formulation in a liquid phase.

10. The method according to claim 1 including the step of applying the formulation in a solid phase.

11. A method to control at least one of fruit abscission, color and sugar content by inducing the synthesis of ethylene and polyamine, the method comprising the steps of applying a formulation containing a 2-hydroxy-4-methylthiobutanoic acid to the leaves of fruiting plants; inducing ethylene and polyamine synthesis; and stimulating a fruit maturation process.

12. A method according to claim 11, wherein inducing polyamine synthesis includes inducing putrescine synthesis.

13. A method for controlling fruit maturation, comprising:
(a) applying a formulation to the leaves of fruiting plants, so as to induce the synthesis of at least one member selected from the group consisting of ethylene and polyamine;
(b) wherein the formulation includes at least one of 2-hydroxy-4-methylthiobutanoic acid, a salt of 2-hydroxy-4-methylthiobutanoic acid, an ester of 2-hydroxy-4-methylthiobutanoic acid, an amide of 2-hydroxy-4-methylthiobutanoic acid and an ether of 2-hydroxy-4-methylthiobutanoic acid, wherein the 2-hydroxy-4-methylthiobutanoic acid has a structure according to the formula $CH_3-S-CH_2-CH_2CH(OR_1)-COR_2$; and
(c) wherein $R_1$ is selected from the group consisting of hydrogen, alkyl moieties and aryl moieties; $R_2$ is selected from the group consisting of hydroxyl moieties, amides of alkyl moieties, esters of alkyl moieties and aryl moieties; and the hydroxyl moiety is an OX moiety and X is selected from the group consisting of monovalent cations, and polyvalent cations.

14. The method for controlling fruit maturation of claim 13, wherein the step of applying includes:
(a) applying a liquid formulation.

15. The method for controlling fruit maturation of claim 13, wherein the step of applying includes:
(a) applying a solid formulation.

* * * * *